(12) United States Patent
Ziola et al.

(10) Patent No.: US 6,851,319 B2
(45) Date of Patent: Feb. 8, 2005

(54) DEVICE AND METHOD DESIGNED FOR ULTRASONICALLY INSPECTING CYLINDERS FOR LONGITUDINAL AND CIRCUMFERENTIAL DEFECTS AND TO MEASURE WALL THICKNESS

(75) Inventors: Steven M. Ziola, Littleton, CO (US); Michael R. Gorman, Englewood, CO (US); William J. Miller, Aurora, CO (US)

(73) Assignee: Digital Wave Corporation, Englewood, CO (US)

( * ) Notice: Subject to any disclaimer, the term of this patent is extended or adjusted under 35 U.S.C. 154(b) by 0 days.

(21) Appl. No.: 09/965,672

(22) Filed: Sep. 26, 2001

(65) Prior Publication Data

US 2002/0078751 A1 Jun. 27, 2002

Related U.S. Application Data

(60) Provisional application No. 60/236,356, filed on Sep. 27, 2000.

(51) Int. Cl.[7] .............................................. G01N 29/26
(52) U.S. Cl. ............................................ 73/622; 73/52
(58) Field of Search ........................ 73/622, 620, 621, 73/637, 638, 52

(56) References Cited

U.S. PATENT DOCUMENTS

| | | | |
|---|---|---|---|
| 4,658,649 A | | 4/1987 | Brook |
| 5,085,082 A | | 2/1992 | Cantor et al. |
| 5,089,997 A | | 2/1992 | Pecukonis |
| 5,461,920 A | * | 10/1995 | Prause et al. .................. 73/622 |
| 5,804,730 A | | 9/1998 | Pfannenstiel et al. |
| 5,955,670 A | | 9/1999 | Goodman et al. |
| 6,125,704 A | | 10/2000 | Wang |
| 6,363,788 B1 | | 4/2002 | Gorman et al. |
| 6,367,328 B1 | | 4/2002 | Gorman et al. |

* cited by examiner

*Primary Examiner*—John E. Chapman
(74) *Attorney, Agent, or Firm*—Jonathan Alan Quine; Quine Intellectual Property Law Group, P.C.

(57) ABSTRACT

Methods and apparatus for ultrasonically scanning cylinders are provided. The methods and apparatus employ as few as one ultrasonic sensor for full immersion scanning and defect detection. Self-centering fixturing spins the cylinder, reducing vibration, allowing for fast ultrasonic scans. To create the 45 degree angle beam shear waves for the circumferential scans, the ultrasonic sensor is offset from the centerline of the cylinder, creating the correct angle for excitation of the shear wave.

26 Claims, 7 Drawing Sheets

DEVICE AND METHOD DESIGNED FOR ULTRASONICALLY INSPECTING CYLINDERS FOR LONGITUDINAL AND CIRCUMFERENTIAL DEFECTS AND TO MEASURE WALL THICKNESS

CROSS-REFERENCES TO RELATED APPLICATIONS

This application is a non-provisional of U.S. Ser. No. 60/236,356, filed Sep. 27, 2000. The present application claims priority to and benefit of U.S. Ser. No. 60/236,356, which is also incorporated by reference in its entirety for all purposes.

FIELD OF THE INVENTION

The invention is in the field of ultrasonic testing of containers, such as cylinders, for cracks, wall thinning, or other defects.

BACKGROUND OF THE INVENTION

Containers can be tested for defects or the presence of foreign bodies in the container using ultrasonic testing. A variety of ultrasonic testing methods and equipment for ultrasonic testing of containers are described in the art, e.g., in U.S. Pat. Nos. 6,125,704, 5,955,670, 5,804,730, 5,089,997, 5,085,082, 4,658,649, and the references cited therein, as well as in recent applications of the inventors and their co-workers, e.g., U.S. Ser. No. 09/613,704; U.S. Ser. No. 09/613,705; U.S. Ser. No. 09/671,405 and U.S. Ser. No. 60/265,171.

Most gas cylinders today are retested with pressurized water (i.e., a "hydrotest"). This method checks expansion, which is related to wall thinning due to corrosion, but does not identify cracks, or other significant cylinder defects.

The present invention overcomes the limitations of the prior art by providing new ultrasonic methods and apparatus for testing cracks and other defects in pipes, cylinders and other containers.

SUMMARY OF THE INVENTION

Apparatus, systems and methods for detecting defects, such as cracks, in containers (e.g., tanks, cylinders, plates, spheres, pipes etc.) are provided. In the apparatus, systems and methods of the invention, a container is immersed in a fluid bath that has a mechanism for rotating the container. An adjustable transmitting/receiving ultrasonic transducer is positioned at one or several positions proximal to the container, with a signal being generated and detected at each position. The container can be rotated as well by the rotation mechanism, providing a great deal of flexibility in positioning of the container relative to the transmitting/receiving ultrasonic transducer. These systems, apparatus and methods are distinct from prior art systems, apparatus and methods which involved positioning of multiple transmitting/receiving transducers at multiple typically fixed positions. Accordingly, the present apparatus, systems and methods are both simpler and more flexible than prior art defect detection systems, methods and apparatus. In addition, the present apparatus/systems are small, simple and robust enough that they are optionally portable (e.g., via pickup truck) and can be brought to a job site, rather than, as in the prior art, needing to bring all of the containers to a central testing facility.

Accordingly, in a first class of embodiments, the invention provides a container defect detection apparatus, system or device. The device includes a fluid tank. A rotatable cup is mounted within the fluid tank. The rotatable cup is configured to receive a first region of a container (e.g., a cylinder). A rotatable cap is configured to receive a second region of the container. An engagement mechanism moves the rotatable cup or rotatable cap towards or away from each other to engage the container. A drive train is coupled to the rotatable cup or the rotatable cap. The drive train turns the rotatable cup or rotatable cap. An adjustable receiving/transmitting transducer is positioned to mount proximal to the container.

In one configuration, a motor is mounted outside of the fluid tank. The motor is typically coupled to a gearbox, which is coupled to an output shaft. The output shaft passes through a bearing housing mounted in a wall of the fluid tank and into contact with the cap. The cap can include a collar made from a deformable material such as rubber to mate with walls of the container. The cap is shaped to mount over a cylinder valve or other protuberance, e.g., at the top of a cylinder or other container.

Commonly, the rotatable cup is coupled to or part of a tailstock assembly which comprises the engagement mechanism. The engagement mechanism can include, e.g., a pneumatic cylinder which moves the rotatable cup into engagement with the container. The tailstock moves towards or away from the drive train. The cup is typically mounted on or integral with the tailstock includes a centering ring (e.g., made from a compliant material such as rubber) to center the container during use of the apparatus.

Optionally, The container defect apparatus includes a receiving transducer display coupled to the receiving transducer. The display displays an output of the receiving/transmitting transducer. Common display formats include a computer screen, e.g., where the receiving transducer is coupled to the computer. Optionally, the apparatus comprises system software for aligning the transmitting/receiving transducer or for analyzing a signal from the transmitting/receiving transducer. The system software (e.g., embodied in the computer) can include software for detecting one or more signal from the receiving transducer, instructions for moving the receiving/transmitting transducer, instructions for directing one or more signal outputs from the receiving/transmitting transducer, or the like.

The receiving/transmitting transducer can be configured to perform a circumferential, longitudinal, or thickness scan of the container. In one configuration, the receiving/transmitting transducer is a right angle transducer.

The receiving/transmitting transducer, which is typically mounted on a search tube, is height and/or angle-adjustable. The search tube is optionally coupled to a rotatable search tube holder. The rotatable search tube holder is optionally coupled to an x-y-z translation mechanism. The mechanism can include, e.g., an x-axis linear table, an x-axis motor which drives the search tube holder along the x-axis linear table, an x-axis encoder which tracks motion of the search tube holder along the x-axis linear table, a y-axis linear table, a y-axis motor which drives the search tube holder along the y-axis linear table, a y-axis encoder which tracks motion of the search tube holder along the y-axis linear table, a z-axis linear table, a z-axis motor which drives the search tube holder along the z-axis linear table, a z-axis encoder which tracks motion of the search tube holder along the z-axis, and/or the like.

Commonly, the fluid tank is partly filled with a coupling fluid such as water. A container is optionally mounted submerged in the water between the rotatable cap and the rotatable cup. Common container configurations include cylinders comprising cylinder valves or other protuberances at a top region of the cylinder.

In addition to apparatus, devices and systems, the invention includes methods of testing for the presence of a container defect, e.g., using the apparatus, devices and systems. In the methods, a container is immersed in water (e.g., in the tank of the apparatus noted above). The container is spun in the water. An ultrasonic transmitting/receiving transducer is moved into proximity with a first circumferential region of the container, which is located at a first angle relative to a central axis of the container. The ultrasonic transmitting receiving transducer is moved along the first circumferential region for a first length (e.g., from the top to the bottom of a cylinder) while transmitting a first set of ultrasonic pulses from the transmitting/receiving transducer into the container. A first set of signals resulting from the first set of ultrasonic pulses are detected. The ultrasonic transmitting/receiving transducer is moved into proximity with a second circumferential region of the container. The ultrasonic transmitting receiving transducer is moved along a second length of the second circumferential region while transmitting a second set of ultrasonic pulses from the transmitting/receiving transducer into the container. The second circumferential region is at a second angle relative to the central axis of the container, and the first and second angles are different. A second set of signals resulting from the second set of ultrasonic pulses are detected. The first and second detected sets of signals are then analyzed to establish whether a defect is present. Again, the apparatus noted above can be used in the practice of the methods herein.

As noted, the apparatus used in the present invention is optionally portable. Thus, in one class of embodiments, the methods of the invention include transporting the container defect detection apparatus to a site proximal to the container, prior to mounting the container in the container defect detection apparatus.

In one class of embodiments, the transmitting/receiving transducer is moved into proximity with the first circumferential region of the container such that a 45 degree shear wave is propagated in a wall of the container. The transmitting/receiving transducer can be moved into proximity e.g., above or below a central axis of the container. Longitudinal, circumferential and thickness scans can all be performed according to the methods of the invention.

Optionally, the receiving/transmitting transducer is mounted on a search tube which is coupled to a rotatable search tube holder, where the rotatable search tube holder is coupled to an x-y-z translation mechanism which includes an x-axis linear table, an x-axis motor which drives the search tube holder along the x-axis linear table, and x-axis encoder which tracks motion of the search tube holder along the x-axis linear table, a y-axis linear table, a y-axis motor which drives the search tube holder along the y-axis linear table, a y-axis encoder which tracks motion of the search tube holder along the y-axis linear table, a z-axis linear table, a z-axis motor which drives the search tube holder along the z-axis linear table, and a z-axis encoder which tracks motion of the search tube holder along the z-axis. In this embodiment, the receiving/transmitting transducer is optionally positioned proximal to the first or second circumferential region by engaging the x-axis motor, the y-axis motor, and/or the z-axis motor. Similarly, the receiving/transmitting transducer is moved along the first or second length of the first or second circumferential region by engaging the x-axis motor, the y-axis motor, and/or the z-axis motor. The receiving/transmitting transducer is optionally moved with the x-y-z translation apparatus, which is controlled by a computer operably coupled to the x-axis encoder, the y-axis encoder, and the z-axis encoder.

Commonly, the ultrasonic transmitting/receiving transducer is moved into proximity with a third, fourth, fifth or additional circumferential region of the container. Thus, in one embodiment, the ultrasonic transmitting receiving transducer is moved along the third, fourth, fifth, or additional circumferential region for a third, fourth, fifth or additional length while transmitting a third, fourth, fifth or additional set of ultrasonic pulses from the transmitting/receiving transducer into the container. The relevant set of signals resulting from the set of ultrasonic pulses is detected, providing an indication of the presence or absence of a container defect.

The above apparatus can be formed as a kit or as components of a kit. For example, one or more of the apparatus components can be packaged together, e.g., with packaging materials, instructions for the practice of the methods herein, packaging containers and/or the like.

BRIEF DESCRIPTION ON THE FIGURES

FIG. 1, Panels A and B are schematic drawings of a system of the invention. Panel A is a top view. Panel B is a front view.

DETAILED DISCUSSION

Figure 1A:
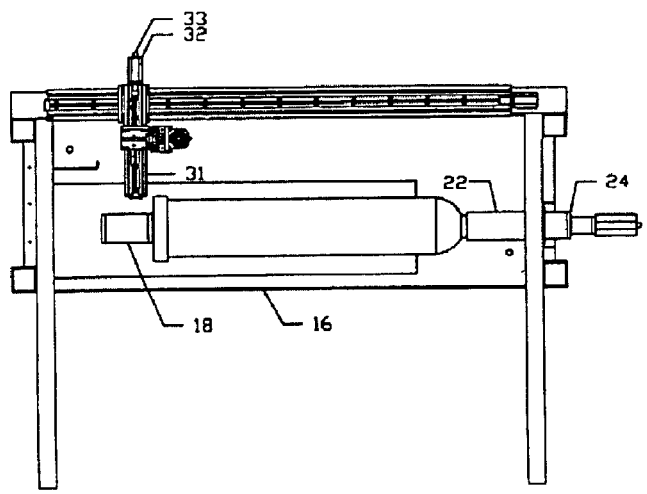

The present invention provides a description of devices/apparatus/systems and methods designed to meet Department of Transportation (DOT) requirements for the ultrasonic retesting of containers (such as cylinders) for longitudinal and circumferential defects and to measure container wall thickness. DOT requires, e.g., that cylinders used for over-the-road transportation of pressurized gases and liquids be retested at periodic intervals to ensure that no defects of a critical size exist in the cylinders.

Most cylinders today are retested with pressurized water, a test generally referred to as a "hydrotest." This inspection method checks expansion of the cylinder, which is related to wall thinning due to corrosion, but this inspection method does not identify cracks in the cylinder. Another disadvantage of the hydrotest is that it introduces water into the cylinder, which causes corrosion, as well as container contamination. The cylinder must then be cleaned before the cylinder can be filled, e.g., with a high purity gas. In contrast, with the ultrasonic method herein, no water is introduced into the cylinders or other containers. Furthermore, the cylinders don't have to be devalved. Eliminating the need for devalving saves the expense, effort and dangers of offloading gases, as well as the associated problems such as leaks, which arise upon revalving.

A novel approach to scanning cylinders such as those commonly used to deliver industrial gases like oxygen and nitrogen is provided by the present invention. An advantage of using the ultrasonic inspection methods of the invention is that small cracks can be detected long before they become critical to cylinder integrity. Although often discussed herein simply in terms of cylinders for convenience and illustration, it will be recognized that pipes, tanks, plates, spheres and other container structures can be tested using the methods and devices herein. That is, the methods herein are suitable to a variety of container configurations (pipes, spheres, plates, tanks, etc.) and are especially applicable to cylindrical objects like gas cylinders and pipes.

Cylinders and other containers are typically made of steel but can also be aluminum or some other metal (or even certain plastics or other polymers) depending on the application. The ultrasonic scanning systems herein are optionally used to inspect steel and aluminum cylinders, especially for cracks that may arise in service.

Cracks in container walls can be oriented axially or circumferentially. In either case, the crack surface can be tilted away from perpendicular to the cylinder surface, which changes the reflection intensity of a delivered ultrasonic beam, depending on the angle between the beam and the crack. In prior art ultrasonic detection methods, a standard 45 degree angle beam shear wave inspection is typically done from two directions relative to normal. Wall thickness is measured by pulse-echo reflections with a transducer normal to the surface. Thus, to accomplish an inspection using prior art ultrasonic methods, five transducers are used: Two opposing transducers for axial cracks and two opposing transducers for circumferential cracks, plus a normal transducer for determining wall thickness. That is, the prior art uses at least five transducers in a fixed arrangement in a scanning head that moves over the surface of the cylinder while the cylinder is rotated.

There are two drawbacks to this prior art approach; the first is that each sensor has its own electronics for signal generation and reception, leading to high expense and complexity. The second is that the sensors are typically mounted in a "shoe" at the various angles required for defect detection, and a gap is left between the sensor face and the face of the shoe. This gap is flooded with water to couple the ultrasound into the cylinder wall. If the cylinder surface is rough or the cylinder is out-of-round, the shoe loses contact with the cylinder surface and the water leaks out of the gap in the shoe. As a result, the sound is not coupled into the cylinder. Transducers have also been put inside fluid-filled rubber wheels that can roll on the cylinder surface. This approach has the same problems as the "shoe" approach.

To ultrasonically inspect the cylinder, the "shoe" is translated down the length of the cylinder as the cylinder is spun. Many ultrasonic pulses are launched and received as the "shoe" (the sensors can both send and receive) moves, so that in reality a helical scan pattern is achieved. In previously described methods, the cylinder is placed on rubber rollers and spun. In these methods, the rollers are attached to a drive motor which spins them, which in turn spins the cylinder. These methods rely on frictional forces between the rubber rollers and the cylinder to spin the cylinder. If the friction is not great enough, the cylinder slips.

In this invention, multiple scans are accomplished with a single transducer using multiple passes. To achieve this, the cylinder is immersed in a coupling fluid (e.g., water). The apparatus described herein engages the cylinder with a new fixturing arrangement, spinning the cylinder in the fluid while maintaining the sensor/cylinder relative positioning. The sensor position is uniquely adjusted to excite the various wave modes required for the scans.

By immersing the cylinder in coupling fluid, such as water, the coupling problems associated with previously described shoe and wheel methods are eliminated. Water completely surrounds the cylinder, and coupling is never lost. In the full immersion methods herein, the ultrasonic sensor never needs to contact the cylinder.

DESCRIPTION OF EXAMPLE EMBODIMENTS

Figure 1B:
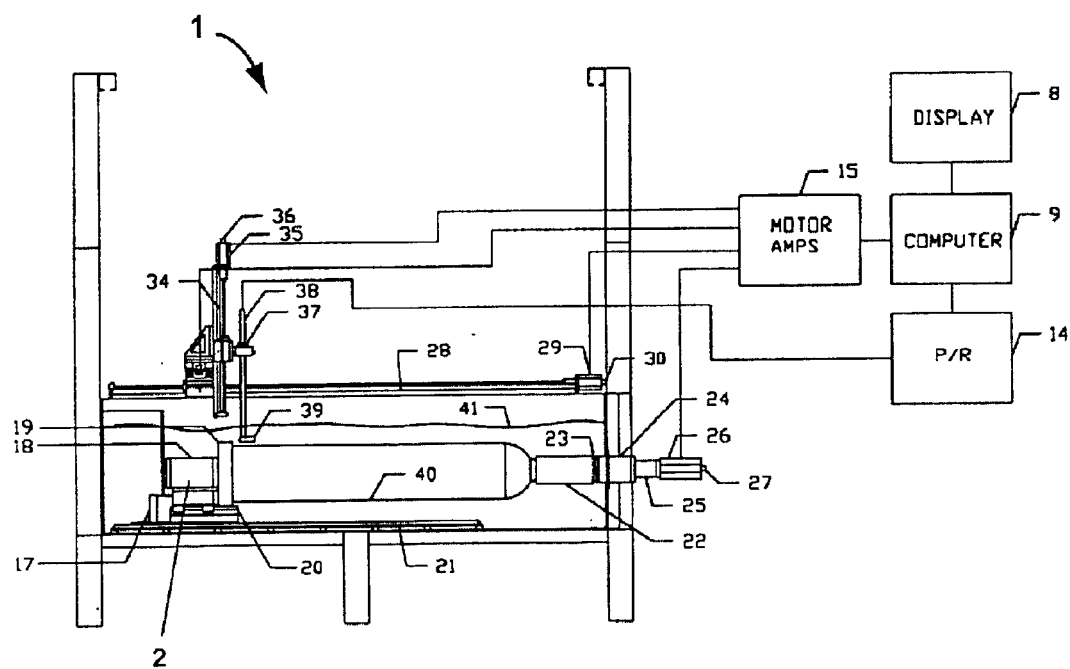
Figure 2:
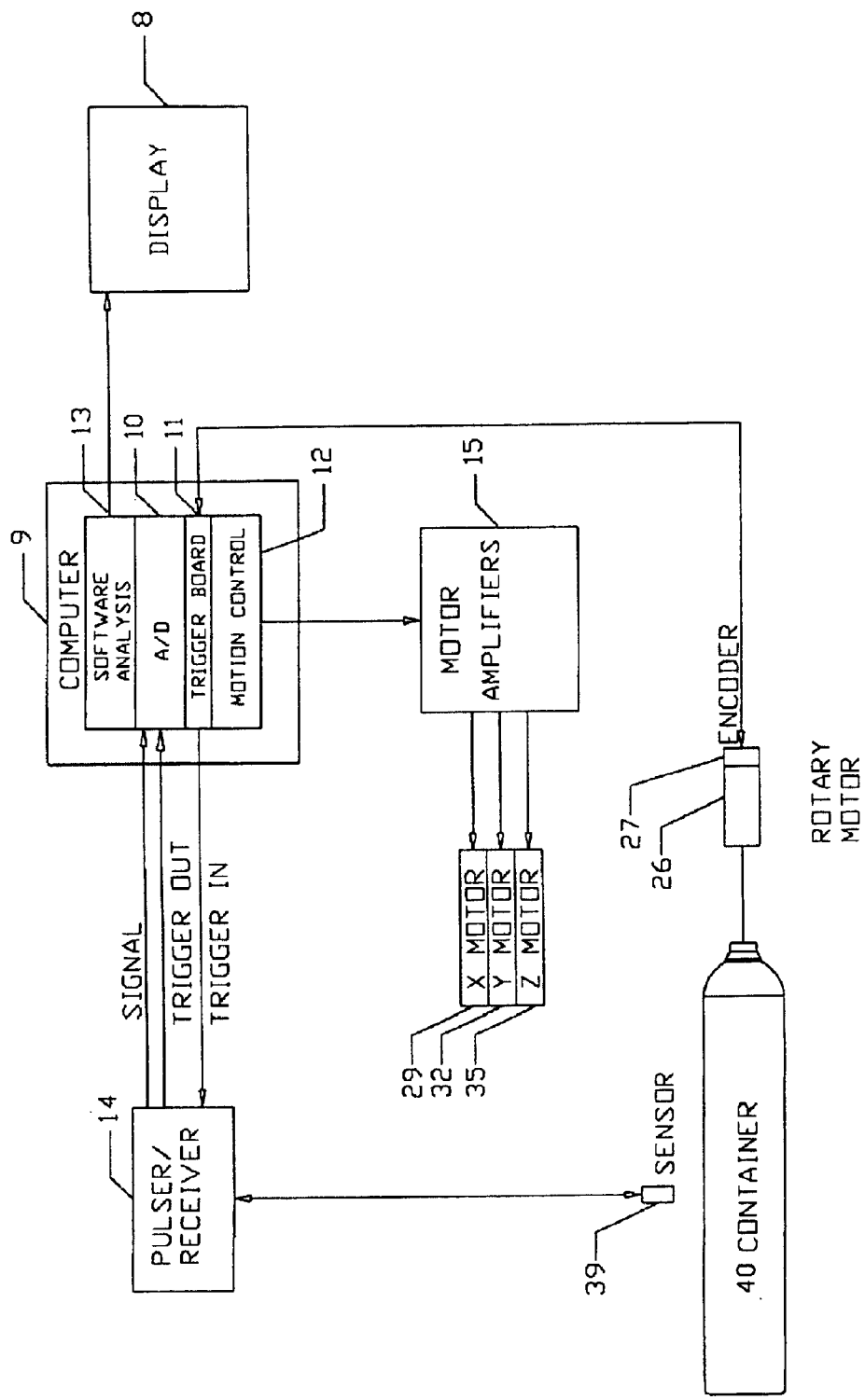
FIG. 2 is a block diagram of the electronic hardware and operation.
Figure 3:
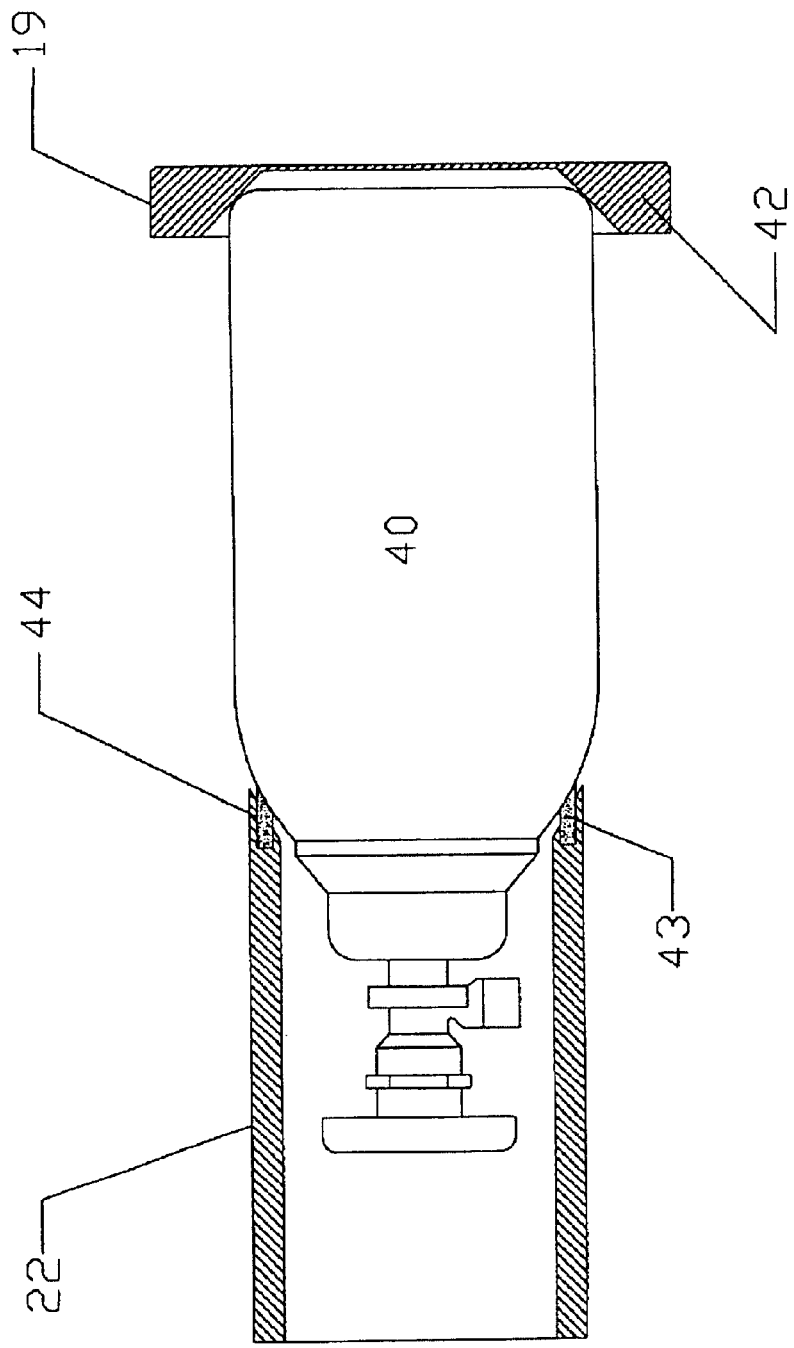
FIG. 3 is a schematic drawing of a self-centering fixture for spinning a cylinder.

FIGS. 1, 2 and 3 provide an example apparatus of the invention. Example apparatus 1 includes display 8, computer 9 (which typically includes A/D converter 10, trigger board 11, motion control 12, and software/analysis module 13), pulser/receiver module 14, motor amplifiers 15, tank 16, pneumatic cylinder 17, tailstock assembly 2 (which typically includes, e.g., bearing housing 18, cup 19, linear slide 20, and tailstock linear slide 21), self-centering cap 22, output shaft 23, bearing housing 24, gear box 25, rotary motor 26, rotary motor encoder 27, x-axis linear table 28, x-axis motor 29, x-axis encoder 30, y-axis linear table 31, y-axis motor 32, y-axis encoder 33, z-axis linear table 34, z-axis motor 35, z-axis encoder 36, rotatable search tube holder 37, search tube 38, ultrasonic sensor 39, container 40, coupling fluid 41, centering ring insert 42, rubber collar 43, and machined groove 44.

When in use, the tank 16 is filled with coupling fluid 41 (e.g., water). Container 40 is placed in the tank between cup 19 and self-centering cap 22. Pneumatic cylinder 17 is then activated, moving the tailstock assembly along linear slide 20. This forces the container into intimate contact with cup 19 and self-centering cap 22. Various lengths of cylinders are accommodated by adjusting the tailstock location along tailstock linear slide 21 and locking the tailstock assembly into place. Bearing housing 18 allows cup 19 to spin.

Container 40 is spun by activating rotary motor 26. Rotary motor 26 is attached to gear box 25. Gearbox 25 is attached to output shaft 23 through bearing housing 24, and self-centering cap 22 is attached to output shaft 23.

Ultrasonic sensor 39 is held in position by being attached to rigid search tube 38. Search tube 38 is mounted in rotatable search tube holder 37, which is then attached to z-axis linear table 34. Ultrasonic sensor 39 is positioned relative to container 40 by activating x-axis motor 29, y-axis motor 32, and z-axis motor 35. The motion is constrained by x-axis linear table 28, y-axis linear table 31 and z-axis linear table 34. X-y-z position of the sensor is determined by encoder outputs of x-axis encoder 30, y-axis encoder 33, and z-axis encoder 36. Sensor position is read by computer 9 using motion control 12 hardware. Motor amplifiers 15 provide power to the motors.

As container 40 is spun, ultrasonic sensor 39 is translated the length of container 40 by x-axis linear table 28. The spinning and linear translation create a helix down the length of the container. The rotary position of the container is determined by the output of the rotary motor encoder 27. Output of rotary encoder 27 is read by a counter on trigger board 11 and used to trigger pulser/receiver module 14. At specific intervals determined by the user, a high voltage electrical pulse from pulser/receiver module 14 is sent to ultrasonic sensor 39. This creates an ultrasonic pulse that propagates through coupling fluid 41 and into a wall of container 40. The pulse echoes back from the wall of container 40, and is detected by ultrasonic sensor 39. Ultrasonic sensor 39 sends a signal to pulser/receiver module 14, which amplifies and filters the received signal and sends a trigger pulse to A/D converter 10. The signal is then digitized by A/D converter 10, and then stored in an electronic format for analysis by software 13.

Figure 7:
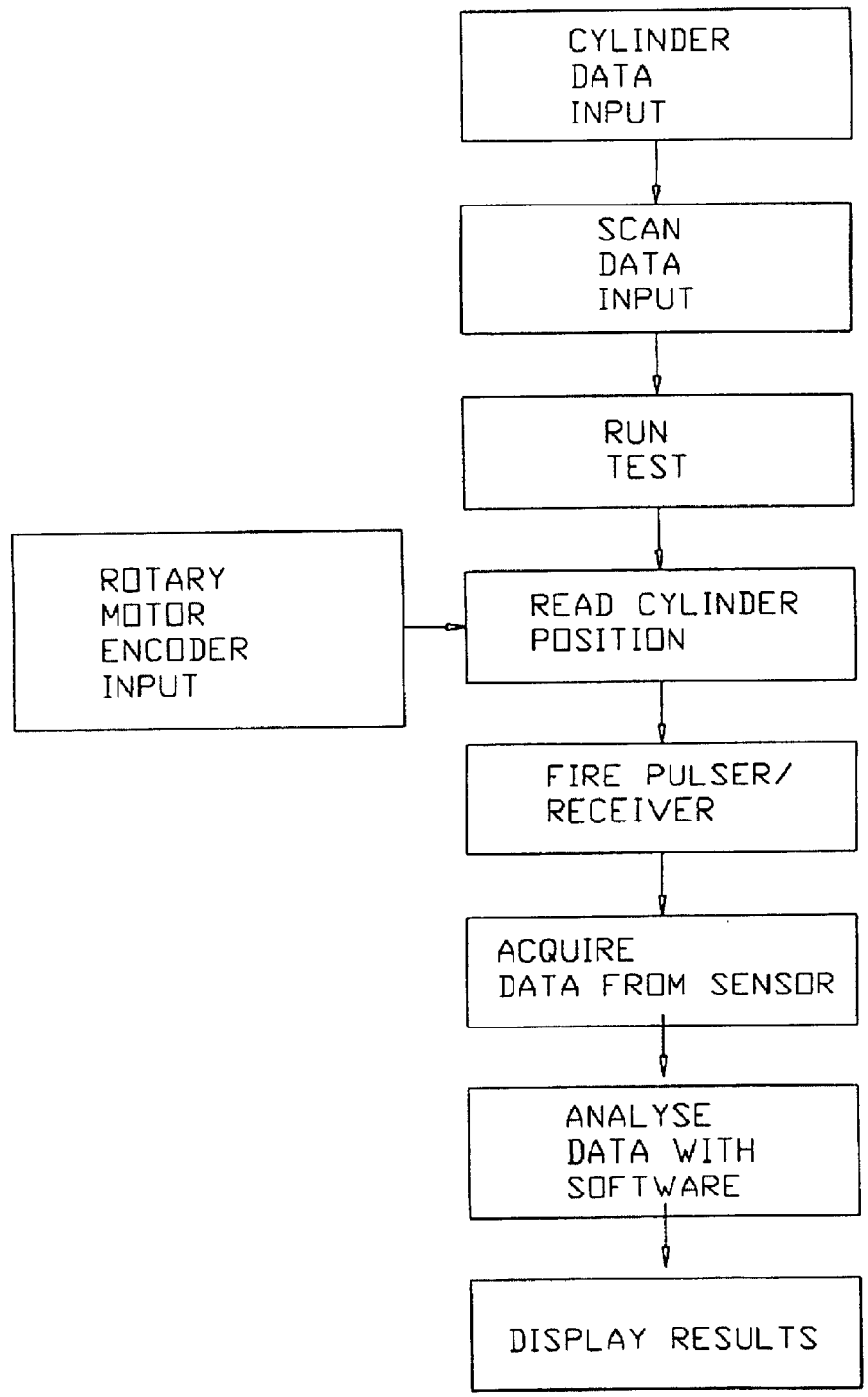
FIG. 7 is a flow chart of an example software operation.

FIG. 7 shows the flow chart of the software operations. The software is used to control motion of the system, data acquisition, and data analysis. The motion control is performed by data input by the operator. Container length, diameter, minimum wall thickness and material properties are input into the software. The rotation speed, scanning resolution, scan start and stop positions, A/D converter rate, data acquisition window length, signal delay, and sensor offset angle (see, FIG. 5) are also input into the software. After the scanning data is input into the software, the operator can scan a container. The software then reads the positions of the various motors and fires the pulser/receiver. The software acquires the data from the ultrasonic inspection. The data is then analyzed for thickness and defect information and the results are displayed.

Figure 4:
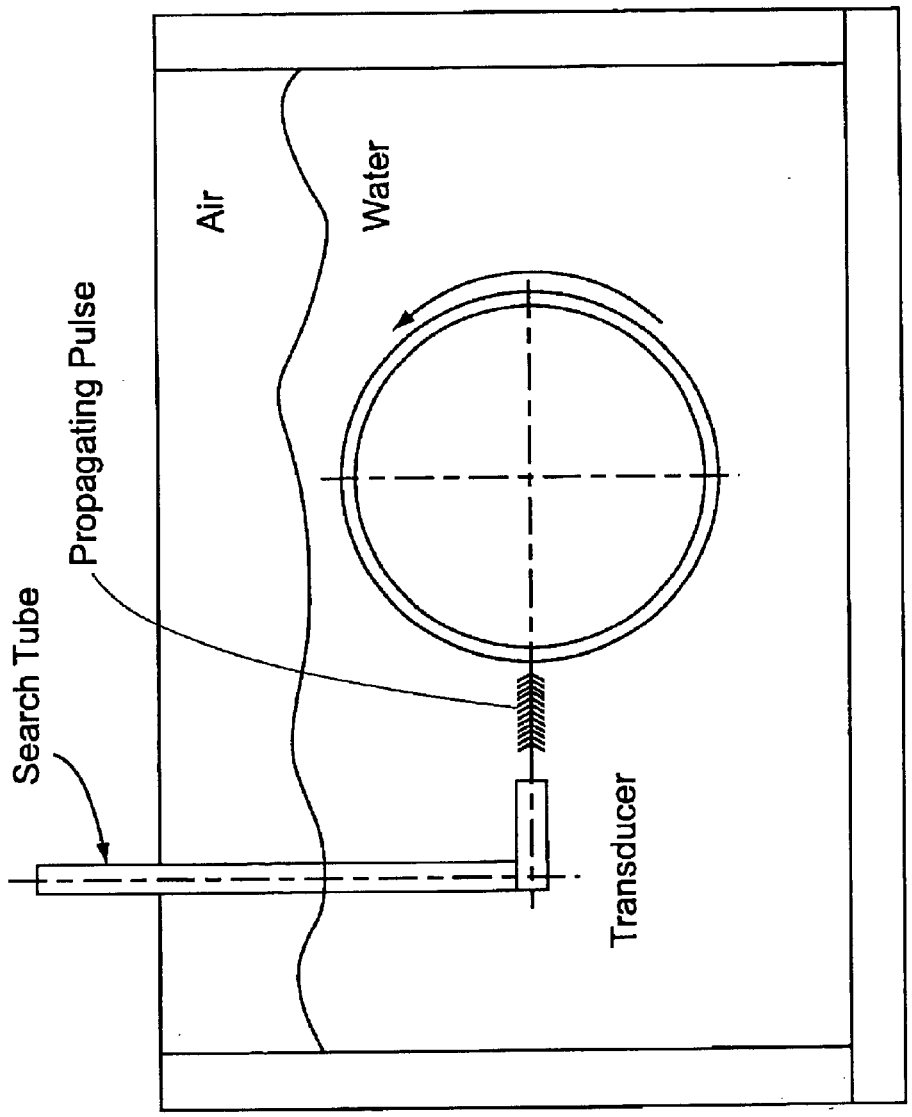
FIG. 4 is a schematic showing a relationship between the search tube, transducer, water and air during ultrasonic thickness scanning according to the present invention.

For the thickness scan, sensor 39 is positioned normal to the container, as shown in FIG. 4, by software 13 through motion control 12 hardware.

Figure 5:
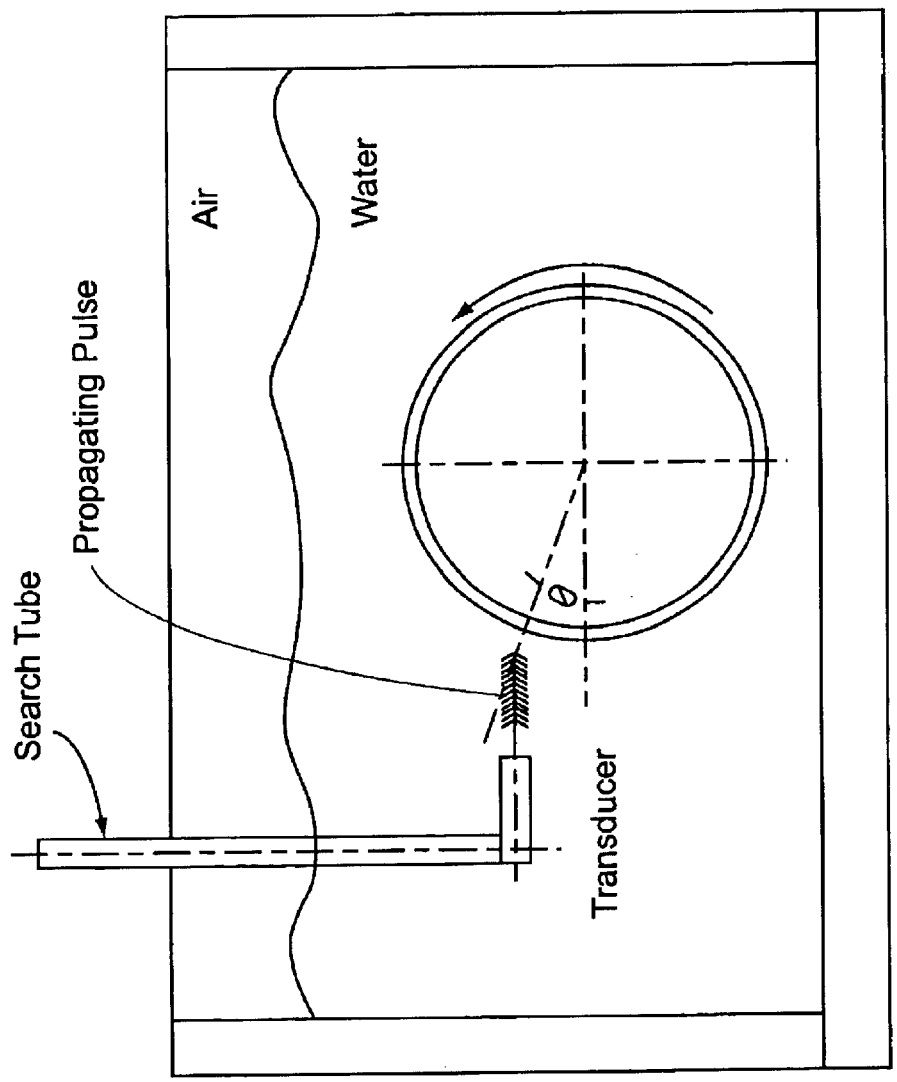
FIG. 5 is a schematic showing a relationship between the search tube, transducer, water and air during ultrasonic circumferential scanning according to the present invention.

To excite a 45-degree angle beam shear wave for circumferential scans, sensor 39 is offset from the centerline, as shown in FIG. 5, by software 13 through the motion control 12 hardware.

Figure 6:
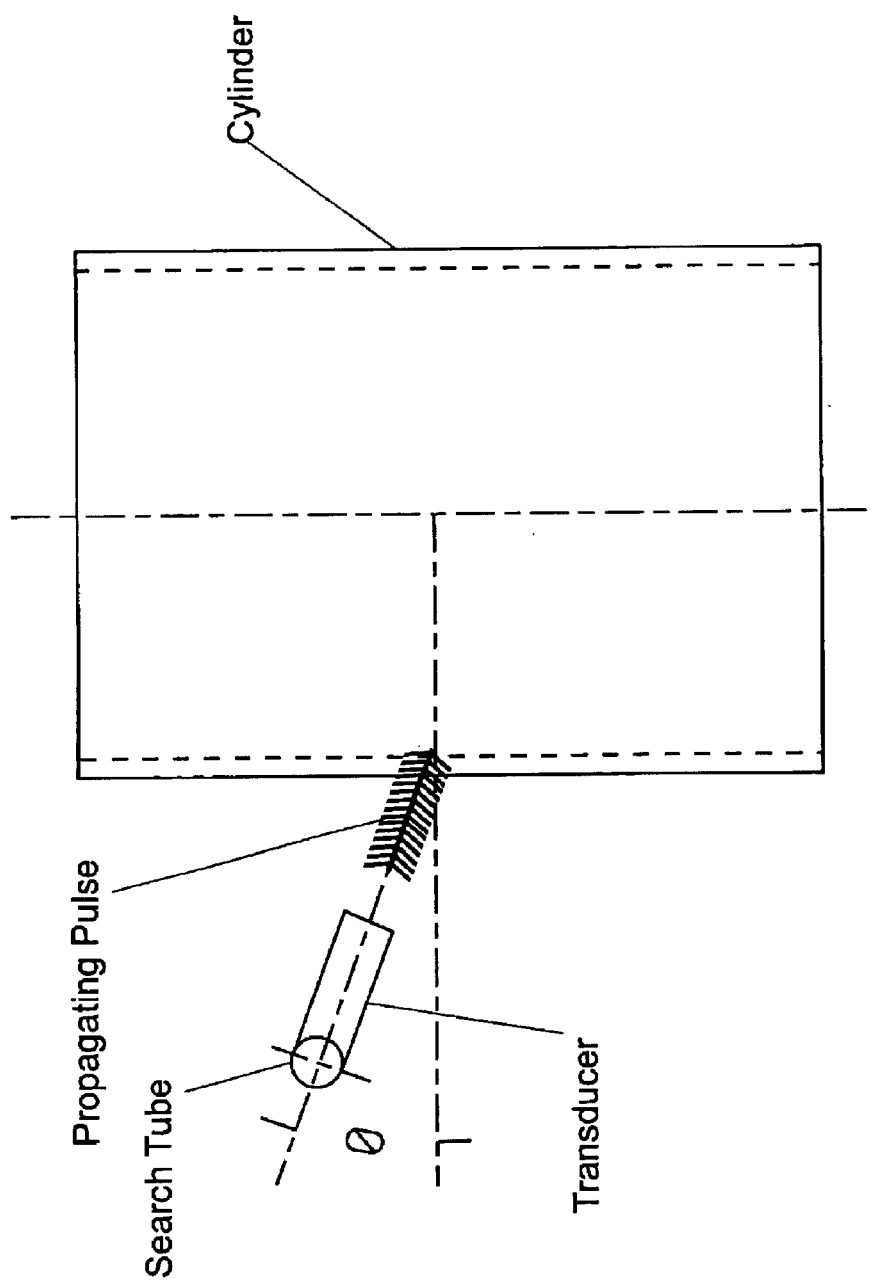
FIG. 6 is a schematic showing a longitudinal scanning arrangement (top view).

To excite a 45-degree angle beam shear wave for the axial scans, sensor 39 is rotated in rotatable search tube holder 37 to create the correct angle, as shown in FIG. 6, manually by the operator.

Details for cup 19 and self-centering cap 22 are shown in FIG. 3. When pneumatic cylinder 17 is activated, the bottom end of the container is forced into centering ring insert 42, and rubber collar 43. The rubber collar is contained in machined groove 44. Self-centering cap 22 fits over the valve in the container.

The apparatus is specially designed to ensure that the cylinder is held in place with respect to the ultrasonic sensor while it is being spun. Rubber rollers will not typically work with a full immersion system, as the cylinder will typically float, eliminating the frictional force required to spin the cylinder. According to the present invention, the cylinder is captured between two centering fixtures and then spun. The centering fixtures consist of a cup and a cap, e.g., as set forth in FIG. 3. The cup consists of an interchangeable centering ring made of UHMW polyethylene or a similar material, mounted in an aluminum (or comparable material) outer ring. The centering ring is tapered to accept various diameter cylinders. A completed tailstock combines with the cap and output shaft to allow the cylinder or other container to self-center. The cylinder is axially clamped, e.g., using a pneumatic cylinder. The cap is made of aluminum with a machined groove that can accept a rubber collar. The cap has tapered edges on both the OD and ID that are staggered above and below the groove. A compliant collar is inserted into the groove and extends beyond the tapered edge of the cap. This allows the collar to deform in a particular way. The collar uses rubber or a similarly compliant material to conform to the cylinder shoulder/dome area. This prevents precession (slippage) so it holds location and minimizes vibration when the cylinder rotates. The domes on the cylinders are formed by forcing the heated cylinder cup into a die, and spinning the cylinder. By clamping on the dome area, the cylinder is centered, as manufactured. By minimizing the vibration in this way, the cylinder can be spun faster than prior art methods, resulting in faster scans. The rubber collar also keeps the metal cap from contacting the cylinder, and thus possibly damaging the cylinder. The cap is attached through a keyway to the drive motor. In an alternate embodiment, the cap can be coupled to the drive train through a drive cone (e.g., a rubber cone that mates with the cap and the drive train). However, if the cap is attached to the drive train via a keyway, the cylinder can be spun more rapidly; accordingly, this embodiment is preferred. In either case, the cap fits over the cylinder valve and can be adapted with simple slots to handle a wide variety of valves including those on fire extinguishers. Thus, valves do not need to be removed.

The tank is specially designed to accommodate a range of cylinders from the largest to the smallest in typical commercial use. This is accomplished by allowing the tailstock, e.g., as set forth in FIG. 1, to be able to slide along a guide, and then be locked in place. For cylinders that are longer or shorter, the tailstock can be moved farther from or closer to the cap, accommodating the various cylinder lengths. The movement of the tailstock can be performed manually, or can be automated with pneumatic, hydraulic or servomechanical methods.

The normal thickness scan is done on an axis perpendicular to the surface, e.g., as shown in FIG. 4.

To create the correct angle for the circumferential scans, the circular nature of the cylinder is taken advantage of. This angle can be calculated from first principles, using Snell's Law of refraction, as is well known in the physics literature. The transducer is moved above the cylinder centerline axis until the correct angle to the normal is achieved, whereby a 45-degree angle beam shear wave is created in the cylinder wall, as shown, e.g., in FIG. 5. To get the opposite circumferential direction the transducer is lowered to a similar position below the cylinder centerline axis. The two longitudinal scans are accomplished using a specially designed search tube holder, e.g., as shown in FIG. 6, that is rotated to a precise angle. This can be performed either manually or automated by attaching a motor to the search tube holder. This fixture holds the transducer at the correct angle to create a 45-degree angle beam shear wave scan as the transducer is translated down the length of the cylinder to detect flaws such as pits and cracks.

A simplified and much less expensive scanner than previously available was built and tested to confirm that the single sensor/multiple scan approach would work. Software was written to automate the scanning. All of the A-scan data (the raw signals from the sensor) were captured digitally, and saved to an electronic media for analysis. In this case, the data was stored in computer memory, and then analyzed. It can, of course, be stored to a hard drive, CD, etc. and then analyzed. All defects were easily mapped and displayed for a user on a computer screen.

Typically, system software provides motion control, data acquisition and data analysis. This eliminates much of the complex hardware required to coordinate the motion of the various axes during the scan. That is, many prior art systems use analog electronics to analyze the data. This leaves only a few signal parameters to describe the transient A-scan signal received by the sensor, and the signal cannot be reanalyzed. If there is noise in the signal (e.g., electromagnetic interference) in the analog system, it can be interpreted incorrectly, resulting in false defect detection. By using high-speed A/D boards and acquiring the digital representation of the signal from the sensor, the signal can be re-analyzed, eliminating these false calls. It also reduces expensive analog circuitry, since the analysis is performed in software. Modifications can be made quickly to the software analysis, as opposed to redesigning and manufacturing new analog circuits.

A flow chart of typical software functions is shown in FIG. 7. The data for the cylinder to be tested (diameter, length, wall thickness, material) and scanning parameters (A/D digitization rate, window length, pulses per revolution, rotational speed, helix index, etc) is input into a job that can be recalled. The user selects the appropriate job for the cylinder to be retested and begins the scan. The software monitors the encoder output from the rotary motor and triggers the pulser/receiver to send a pulse to the sensor at the appropriate time, as determined by the scanning parameters. The software then controls the data acquisition board, and Stores the digitized data to an electronic format, suitable for recall of the data. Data analysis routines in the software then analyze the signals for wall thickness and defects, and display the information. Software routines alert the operator to defects that exceed the minimum size criteria.

The system is also more flexible in that different container metals (or other materials) can be accommodated easily, since the changes for the various metals are input into the software, and do not require the manufacture of new hardware. Changing transducers for different frequency scans is simpler and much less costly, and maintenance is reduced significantly since only a single set of electronics for launching and receiving the ultrasonic pulse is needed. The elimination of the bulky "shoe" allows easier scanning of smaller cylinders. Unlike the flooded head systems, no water recirculation systems are needed to supply water to the heads. The small amount of water in the tank is used over and over, thus saving water. The scanner is portable, e.g. by pickup truck. This can reduce or eliminate wasteful transport of empty steel cylinders over hundreds of miles to central retest stations.

It will be appreciated that the above methods and apparatus can be modified for the use of multiple sensor arrays for the scanning of cylinders. That is, although not necessary, it is certainly possible to use more than one transducer/receiver in the system. All of the concepts noted above still apply and, of course, the apparatus for centering and rotating the containers is universally applicable, regardless of the precise transmitters or receivers which are used.

The foregoing description of embodiments of the invention has been presented for purposes of illustration and description. The description is not intended to be exhaustive or to limit the invention to the precise form disclosed, and many modifications and variations are possible in light of the above teaching. Such modifications and variations, which may be apparent to a person skilled in the art, are within the scope of this invention. All patent applications, patents, patent documents and other publications cited herein are incorporated by reference in their entirety for all purposes to the same extent as if each item were so individually denoted.

What is claimed is:

1. A container defect detection apparatus, comprising:
    a fluid tank;
    a rotatable cup mounted within the fluid tank, which rotatable cup is configured to receive a first region of a container;
    a rotatable cap configured to receive a second region of the container;
    an engagement mechanism which moves the rotatable cup or rotatable cap towards or away from each other to engage the container;
    a drive train coupled to the rotatable cup or the rotatable cap, which drive train turns the rotatable cup or rotatable cap; and,
    an adjustable receiving/transmitting transducer positioned to mount proximal to the container.

2. The container defect apparatus of claim 1, wherein the cup comprises a centering ring.

3. The container defect apparatus of claim 1, wherein the cap comprises a rubber collar.

4. The container defect apparatus of claim 1, the drive train comprising:
    a motor mounted outside of the fluid tank, which motor is coupled to a gearbox, which gear box is coupled to an output shaft, which output shaft passes through a bearing housing mounted in a wall of the fluid tank and into contact with the cap.

5. The container defect apparatus of claim 1, wherein the rotatable cap is shaped to mount over a cylinder valve.

6. The container defect apparatus of claim 1, wherein the rotatable cup is coupled to a tailstock assembly which comprises the engagement mechanism.

7. The container defect apparatus of claim 1, wherein the rotatable cup is coupled to a tailstock assembly which comprises the engagement mechanism, which engagement mechanism comprises a pneumatic cylinder which moves the rotatable cup into engagement with the container.

8. The container defect apparatus of claim 1, wherein the engagement mechanism comprises a pneumatic cylinder.

9. The container defect apparatus of claim 1, wherein: the rotatable cup is housed in a tailstock; the engagement mechanism comprises a slide upon which the tailstock moves towards or away from the drive train; and, the drive train is coupled to the rotatable cap.

10. The container defect apparatus of claim 1, comprising a receiving transducer display coupled to the receiving transducer, which display displays an output of the receiving/transmitting transducer.

11. The container defect apparatus of claim 10, wherein the display is a computer screen and wherein the receiving transducer is coupled to a computer, which computer comprises instructions for detecting one or more signal from the receiving transducer.

12. The container defect apparatus of claim 10, wherein the display is a computer screen and wherein the receiving transducer is coupled to a computer, which computer comprises instructions for moving the receiving/transmitting transducer.

13. The container defect apparatus of claim 10, wherein the display is a computer screen and wherein the receiving transducer is coupled to a computer, which computer comprises instructions for directing one or more signal outputs from the receiving/transmitting transducer.

14. The container defect apparatus of claim 1, wherein the receiving/transmitting transducer is positioned above or below the centerline of the container when the container is mounted in the apparatus, to provide a 45 degree shear wave as the search tube holder and transducer is moved along a longitudinal axis of the container.

15. The container defect apparatus of claim 1, wherein the receiving/transmitting transducer is mounted on a search tube holder that holds the transducer at an angle to provide a 45 degree shear wave as the search tube holder and transducer is moved along a longitudinal axis of the container, when the container is mounted in the apparatus.

16. The container defect apparatus of claim 1, wherein the receiving/transmitting transducer is positioned normal to the container, when the container is mounted in the apparatus to provide a longitudinal wave as the search tube holder and transducer is moved along a longitudinal axis of the container.

17. The container defect apparatus of claim 1, wherein the receiving/transmitting transducer is height or angle adjustable with respect to the container, when the container is mounted in the apparatus.

18. The container defect apparatus of claim 1, wherein the receiving/transmitting transducer is mounted on a search tube.

19. The container defect apparatus of claim 18, wherein the search tube is coupled to a rotatable search tube holder.

20. The container defect apparatus of claim 19, wherein the rotatable search tube holder is coupled to an x-y-z translation mechanism which comprises an x-axis linear table, an x-axis motor which drives the search tube holder along the x-axis linear table, and x-axis encoder which tracks motion of the search tube holder along the x-axis linear table, a y-axis linear table, a y-axis motor which drives the search tube holder along the y-axis linear table, a y-axis encoder which tracks motion of the search tube holder along the y-axis linear table, a z-axis linear table, a z-axis motor which drives the search tube holder along the z-axis linear table, and a z-axis encoder which tracks motion of the search tube holder along the z-axis.

21. The container defect apparatus of claim 1, wherein the receiving/transmitting transducer is a right angle transducer.

22. The container defect apparatus of claim 1, wherein the fluid tank is partly filled with water.

23. The container defect apparatus of claim 1, further comprising a container mounted between the rotatable cap and the rotatable cup.

24. The container defect apparatus of claim 23, wherein the container is a cylinder comprising a cylinder valve in the second region, wherein the rotatable cap is a drive collar shaped to mount over the cylinder valve.

25. The container defect apparatus of claim 1, wherein the apparatus is portable.

26. The container defect apparatus of claim 1, wherein the apparatus further comprises system software for aligning the transmitting transducer with respect to the container, when the container is mounted in the apparatus or for analyzing a signal from the transmitting/receiving transducer.

* * * * *